United States Patent [19]
Heinonen

[11] Patent Number: 6,139,506
[45] Date of Patent: Oct. 31, 2000

[54] METHOD FOR MEASURING PULMONARY FUNCTIONAL RESIDUAL CAPACITY

[75] Inventor: Erkki Heinonen, Helsinki, Finland

[73] Assignee: Instrumentarium Oy, Helsinki, Finland

[21] Appl. No.: 09/240,722

[22] Filed: Jan. 29, 1999

[51] Int. Cl.$^7$ ..................................................... A61B 5/08
[52] U.S. Cl. ........................................... 600/532; 600/529
[58] Field of Search ..................... 600/532, 529; 128/200.26, 204.22, 204.23, 200.15

[56] References Cited

U.S. PATENT DOCUMENTS

| | | | |
|---|---|---|---|
| 5,447,165 | 9/1995 | Gustafsson | 600/532 |
| 5,540,233 | 7/1996 | Larddon et al. | 600/532 |
| 5,573,005 | 11/1996 | Ueda et al. | 600/532 |
| 5,887,586 | 3/1999 | Dahlback et al. | 600/532 |
| 5,957,128 | 9/1999 | Hecker et al. | 600/532 |
| 6,010,459 | 1/2000 | Silkoff et al. | 600/532 |

FOREIGN PATENT DOCUMENTS 791327  8/1997  European Pat. Off. .

OTHER PUBLICATIONS

Automated Sulfur Hexafluoride Washout Functional Residual Capacity Measurement System For Any Mode of Mechanical Ventilation as well as Spontaneous Respiration,, Thomas D. East, PhD. et al, Critical Care Medicine, vol. 18, No. 1, 1990, pp. 84–91.

Determination of Lung Volume in the ICU, H. Burchardi, H. Wrigge and M. Sydow, Yearbook of Intensive Care and Emergency Medicine, Springler ISBN 3–540–63798–2, 1998.

Medical Instruments and Devices, The Biomedical Engineering Handbook, Joseph D. Bronzino, IEEE Press, pp. 1236–1239, 1995.

Primary Examiner—Max Hindenburg
Assistant Examiner—Brian Szmal
Attorney, Agent, or Firm—Andrus, Sceales, Starke & Sawall

[57] ABSTRACT

A method for determining pulmonary functional residual capacity (FRC). A given amount of indicator gas is delivered into the breathing gases flowing into the lungs of a subject in a selected number of sequential breaths. The amounts of indicator gas delivered during the selected number of breaths are summed to provide a cumulative total ($\Sigma V_{in}$). The amount of indicator gas exhaled in the number of sequential breaths is summed to provide a cumulative total ($\Sigma V_{out}$). An indication of the concentration of indicator gas in the lungs of the subject ($F_{ET}$) is obtained for said two or more breaths. Using the quantities ($\Sigma V_{in}$), ($\Sigma V_{out}$), and ($F_{ET}$) as measured variables, at least two measured value data sets are formed in which the product of the indicator gas concentration ($F_{ET}$) and a regression coefficient comprising the functional residual capacity (FRC) plus the product of the cumulative total of exhaled indicator gas ($\Sigma V_{out}$) and a regression coefficient K equals the cumulative total of the delivered indicator gas ($\Sigma V_{in}$). Multi dimensional regression analysis is carried out using the data sets to obtain values for K and FRC fitted to said data sets. The value FRC so obtained is a determination of function residual capacity.

37 Claims, 5 Drawing Sheets

METHOD FOR MEASURING PULMONARY FUNCTIONAL RESIDUAL CAPACITY

BACKGROUND OF THE INVENTION

The present invention relates to an improved method for measuring the pulmonary functional residual capacity (FRC) of a subject. Functional residual capacity (FRC) is the gas volume remaining in the lungs after unforced expiration or exhalation.

Two methods are currently used to measure functional residual capacity. In one such method, the subject is positioned in a gas tight body box. The subject's airways are sealingly connected to a breathing conduit connected to the exterior of the body box. The conduit has a valve or other means for temporarily closing the conduit. By measuring lung pressures and pressures in the box, at various respiration states and valve conditions, the functional residual capacity can be determined.

However, this method is not suitable for critically ill and/or artificially ventilated patients because spontaneous breathing action and movement of the patient into and out of the body box are required.

The inert gas wash-out measurement technique for functional residual capacity is based on a determination of the amount of gas exhaled from the subject's lungs and corresponding changes in gas concentrations in the exhaled gas. The gas used for the measurement is inert in the sense that it is not consumed during respiration. This gas is also sometimes called a "marker," "tracer," or "indicator" gas. Typical gases used for functional residual capacity measurements are nitrogen, helium, argon, and sulfur hexafluorine ($SF_6$). Nitrogen is used to describe the technique below.

Initially, the lung volume forming the functional residual capacity contains nitrogen in the same percentage as in air, i.e. approximately 80%. In the wash-out measurement technique, the subject commences breathing pure oxygen. With each breath, nitrogen in the lungs is replaced by oxygen, or, stated conversely, the nitrogen is "washed out" of the lungs by the oxygen. The breathing of pure oxygen could continue until all nitrogen is washed out of the lungs. In practical uses of the technique, the breathing of pure oxygen continues until the nitrogen concentration in the exhaled respiratory gases falls below a given concentration.

The gist of the inert gas wash-out technique is to determine the volume of inert or indicator gas washed out of the lungs, and, knowing the initial concentration of indicator gas in the lungs, to compute the functional residual capacity of the lungs from these quantities. In the case of air and nitrogen, the initial concentration of nitrogen in the lungs is 80%. The washed out nitrogen volume is, therefore, 80% of the lung volume. Thus, if the washed out nitrogen amount is 1,870 ml, the FRC volume is 2337 ml (i.e., 1,870 divided by 0.8).

A straightforward way to carry out the inert gas wash-out method for determining FRC volume is described in the Biomedical Engineering Handbook, CRC Press, 1995, ISBN 0-8493-8346-3, pp. 1237–1238. In the method therein described, the subject inhales pure oxygen and exhales into an initially empty collection reservoir until the exhaled nitrogen concentration falls below a desired concentration, for example, an end tidal value below 1%. The exhaled volume is then measured and the concentration amount of nitrogen in the exhaled volume is determined, as by means of a spectrometer. The product of the exhaled gas volume and the nitrogen concentration is the amount of nitrogen exhaled. As noted above, the latter quantity divided by the original concentration of nitrogen (0.8 in the case of air) gives the FRC volume. The foregoing determination can be expressed as $$FRC = \frac{F_{N2} \times V_E}{0.80} \qquad (1)$$

where $F_{N2}$ is the concentration of nitrogen in the collected gas; $V_E$ is the volume of exhaled gases and 0.80 is the concentration of nitrogen in air.

However, the foregoing method, while simple, requires bulky equipment to collect tens of liters of exhaled gas. It is further necessary to ensure that there are no leaks in the system so that the patient inhales only oxygen and breathes only into the collection reservoir.

Instead of measuring the amount of inert gas which is exhaled into a collecting reservoir, the exhaled gas quantity can be obtained by integrating the product of instantaneous exhaled gas flow and the corresponding inert gas concentration. Such a measuring method is described in Crit Care Med, Vol. 18, No. 1, 1990, pp. 84–91 and in the Yearbook of Intensive Care and Emergency Medicine, Springler, 1998 (ISBN 3-540-63798-2), pp. 353–360.

This approach can be expressed as $$FRC = \frac{\int_{tB}^{tE} -\dot{Q}(t) \cdot F_{N_2}(t) dt}{F_{N_2}(t_B) - F_{N_1}(t_E)} \qquad (2)$$

where $\dot{Q}$ is exhaled gas flow, $t_B$ is the beginning time of the wash-out, and $t_E$ is the end time. The denominator of the equation notes that it is most accurate to say that the inert gas in the lungs is the difference between the beginning value $F_{n2}(t_B)$ and the end value $F_{n1}(t_E)$.

However, this technique experiences difficulties because of the need for accurate synchronization of the gas flow and concentration measurements. This may be difficult to obtain due to different delays in the different sensors for flow and for concentration. Depending on the indicator gas being used, the technique also experiences a delay caused by the wash-in of the indicator gas prior to starting the measurement. And, the measurement can be disturbed by leakages in the measurement system. This may occur, for example, with pediatric patients where unsealed intubation tubes are commonly used or when a breathing mask is imperfectly sealed to the subject. In such a case, an unmeasurable amount of the indicator gas escapes from the amount used to determine functional residual capacity.

By analogy to the above described wash-out measurement technique, it is also possible to use a wash-in of indicator gas for measurement of functional residual capacity. Such a technique and apparatus is described in European Patent Publication EP 791,327. This technique also incorporates instantaneous measurement of gas flow and corresponding indicator gas concentration and integration of the product thereof to determine indicator gas quantities. In the wash-in technique, the measurements are carried out for both inhaled and exhaled amounts of indicator gas. However, this technique, similar to the wash-out technique, experiences the difficulty of synchronization of the two measurements and a sensitivity to leakages in the system.

Further, all the foregoing techniques require the subject to be ventilated first with one gas, such as air, and then another gas, such as pure oxygen. If the subject whose functional residual capacity is being determined in this manner is a critically ill patient, variation in inspired oxygen concentration may be medically inadvisable or impossible.

BRIEF SUMMARY OF THE INVENTION

It is, therefore, the object of the present invention to provide an improved method for determining functional residual capacity of a subject that avoids the above noted shortcomings of existing techniques/apparatus.

More specifically, it is the object of the present invention to provide such a method that results in only a minimal disturbance of the breathing regimen of the subject, thereby to facilitate obtaining functional residual capacity measurements from a critically ill patient, or similar subject.

Another object of the present invention is to provide such a method that enables an accurate determination of functional residual capacity, not withstanding the presence of leaks, unsealed intubation tubes, and the like, in breathing apparatus associated with the subject. The technique of the present invention is thus capable of obtaining accurate FRC measurements from subjects such as pediatric patients.

The gist of the present invention is to provide a precisely determined amount of indicator gas to the breathing gases inhaled by the subject. In a preferred embodiment of the present invention, the indictor gas may be sulfurhexafluorine ($SF_6$). The presence of such a gas may be easily monitored so that very small quantities of the gas, for example, concentrations less than 1.0%, and even quantities less than 0.5% may be used to determine functional residual capacity. The use of such low concentrations of indicator gas minimizes alterations in the breathing regimen of the subject.

The indicator gas is provided in a manner that insures all the indicator gas will be delivered to the subject's lungs. It is also desired that the indicator gas mix as uniformly as possible with the breathing gases in the subject's lungs. This may be accomplished by injecting a discrete dose of the indicator gas in the breathing gases of the subject. The start of the dose is synchronized with the commencement of inhalation and the dose ends before the lungs are filled, i.e. while the breathing gases are still moving into the lungs of the patient.

The amount of indicator gas exhaled by the subject is measured, as by integrating the product of instantaneous exhalation gas flow and the corresponding concentration of indicator gas during exhalation.

Subtraction of the exhaled amount of indicator gas from the inhaled amount of indicator gas gives the amount of inert gas remaining in the lungs of the subject at the end of exhalation, i.e. the amount of indicator gas in the functional residual capacity (FRC) of the subject's lungs. The concentration of indicator gas in the exhaled gases, for example, the end tidal concentration, can be taken to be the same as the concentration of the indicator gas in the functional residual capacity of the subject's lungs. The volume of the functional residual capacity can thus be determined by dividing the volume of indicator gas remaining in the subject's lungs by the concentration of the indicator gas in the exhaled gases. This is expressed in Equation 3 below.

$$FRC = \frac{V_{in} - \int F \times Q \times dt}{F} \quad (3)$$

where $V_{in}$ is the inhaled amount of indicator gas, Q is the exhalation gas flow, and F is the corresponding indicator gas concentration.

Sequences of breaths and multiple dimensional regression analysis of data sets obtained from the breaths of such sequences are used to enhance the accuracy of the determination of functional residual capacity. Such an analysis incorporates an alterable regression coefficient that insures the accuracy of the functional residual capacity determination, notwithstanding the existence of breathing gas leaks and other sources of error.

Refinements to the above described method of the present invention, for example, compensation for anatomical dead spaces, simplifying assumptions in the determination of the amount of exhaled indicator gas, and the like are set out in the following detailed description.

DETAILED DESCRIPTION OF THE PREFERRED EMBODIMENT

Figure 1:
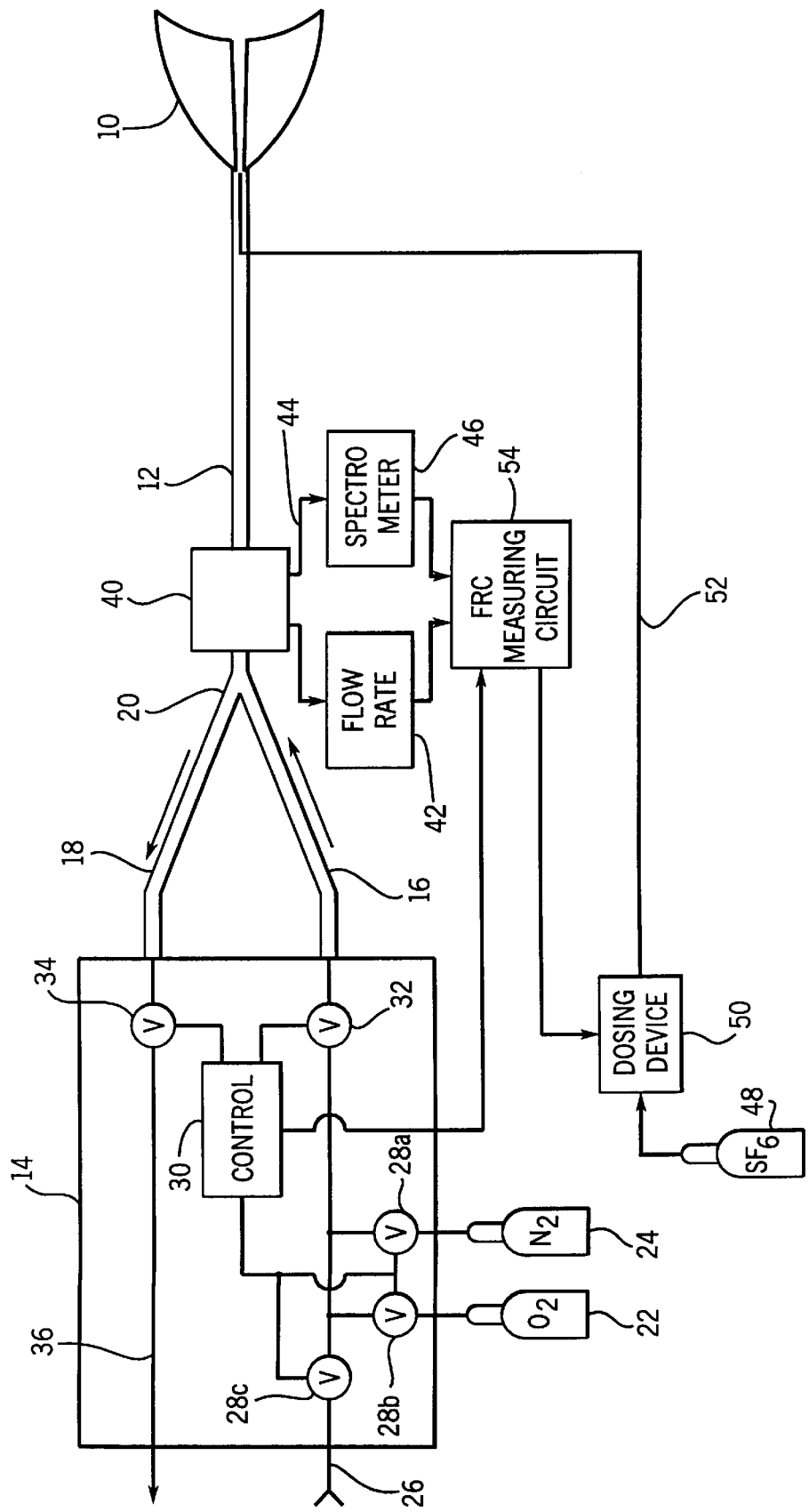
FIG. 1 is a schematic diagram of apparatus suitable for carrying out the method of the present invention.

FIG. 1 shows apparatus suitable for carrying out the method of the present invention for determining the functional residual capacity of a subject's lungs 10. The subject breathes a breathing gas or breathing gases through a breathing circuit including breathing tube 12. Tube 12 may be connected to a face mask for the subject or tube 12 may be an endotracheal tube placed in the trachea of the subject. The subject may breath spontaneously or with the assistance of a respirator or other breathing apparatus 14 through breathing circuit components comprising an inhalation limb 16 and an exhalation limb 18 connected through Y connector 20 to breathing tube 12.

If a respirator is being used, the breathing gases for the subject may be provided from gas supplies such as pressurized gas cylinders 22 and 24, as well as through conduit 26 providing ambient air. Valves 28a, 28b, and 28c, controlled by control 30, determine the composition of gases inhaled by the subject.

Control 30 also determines the rate of breathing, the amount of inhalation gases provided to the patient, the amount of end pressure to which the patient is subjected, and other aspects of the subject's breathing by means of inhalation valve 32 and exhalation valve 34. Inhalation valve 32 is connected to inhalation limb 16. Exhalation valve 34 is connected to exhalation limb 18 and typically discharges the exhaled gases to the atmosphere, as through conduit 36.

The foregoing describes a respirator of generally conventional construction.

A flow sensor 40 is provided in breathing tube 12 or the respirator for determining the gas flow rate in the breathing tube, particularly during the exhalation phase of the respiratory cycle. Flow sensor 40 may be of any suitable type, for example, a pneumotachograph that utilizes the pressure drop across a flow restrictor, a turbine wheel, an anemometer, or the like, to determine the flow. The output of flow sensor 40 is provided to circuitry 42 for converting the physical phenomenon occurring in the flow sensor to a signal indication of the gas flow rate. Flow sensor 40 or breathing tube 12 may also include a connection for sampling conduit 44 connected to a device 46 for determining the concentration of one or more selected components of the gases in breathing conduit 12. Such a concentration determining device may comprise an infrared spectrometer, mass spectrometer, or other suitable means. Alternatively, a gas concentration sensor may be interposed in the breathing circuit to measure gas concentrations in the breathing circuit.

The breathing apparatus shown in FIG. 1 also includes means for providing a precisely determined quantity of an indicator gas into the breathing circuit for the patient. The indicator gas may be provided from a pressurized tank source 48. As noted above, the indicator gas is a gas, such as nitrogen, helium, argon, or as currently deemed preferable, sulphurhexafluorine (SF6). A dosing device, such as an electrically controlled valve 50 is connected to the outlet of indicator gas source 48. Dosing device 50 provides precisely controlled discrete doses or pulses of indicator gas to supply line 52 for provision to breathing tube 12.

Dosing device 50 is controlled by functional residual capacity measuring circuit 54. When a respirator is in use, functional residual capacity measuring circuit 54 receives an input from respirator control 30 for controlling the timing of the provision of the doses of indicator gas to breathing tube 12. Or a sensor may be provided in the breathing circuit for this purpose and connected to circuit 54. The sensor may be a pressure sensor or, depending on the type of sensor employed as flow sensor 40, it may be possible to use flow sensor 40 for this purpose. Functional residual capacity measuring circuit 54 also receives inputs from flow rate circuit 42 and concentration measuring device 46.

To obtain accurate measurement of the functional residual capacity, it is desirable to provide the precise dose of indicator gas into the breathing gases inhaled by the subject in such a way as to ensure that all of the indicator gas dose is delivered into the lungs of the subject. This may be accomplished, for example, by synchronizing the start of the delivery of the measured amount of indicator gas with the start of inhalation by the subject and delivering the indicator gas in a pulse which stops before inhalation stops and the supply of inhaled, breathing gases to the lungs ceases. The sensor, such as a pressure sensor, or flow sensor 40, provided in breathing tube 12 may be used to sense the start of inhalation. Or, when respirator 14 is being used, signals provided by control 30 to functional residual capacity measuring circuit 54 can achieve this result by coordinating the operation of circuit 54 and dosing device 50 with the operation of the respirator.

With the indicator gas delivered at the beginning of inspiration, the effect of leakage in the breathing circuit can be lessened or eliminated. Such leakage is most likely to occur at the end of inspiration or beginning of exhalation when pressure within the lungs is maximum. By delivering the indicator gas at the beginning of inspiration when pressures are still low, leakage does not occur and all the indicator gas is delivered into the subject's lungs. The duration of the indicator gas pulse can be selected in accordance with the breathing cycle of the subject so that delivery of the indicator gas is finished before inhalation stops.

Also, the discharge end of indicator gas supply line 52 may be placed as close to the lungs as possible to assist in delivering the indicator gas to the patient's lungs. For example, if an endotracheal tube is being used, the discharge end of supply line 52 may be placed at the distal end of the endotracheal tube.

It is desired to achieve as uniform mixing as possible of the indicator gas with the breathing gas or gases in the subject's lungs and supplying indicator gas in the foregoing manner assists in obtaining uniform mixing throughout the lung volume of the subject by the time the subject's inhalation is complete. The supply of indicator gas in this fashion also helps to prevent the indicator gas from residing in the upper airways or other non-lung portions of the subject's respiratory system.

Apparatus similar to that shown in FIG. 1 is disclosed in detail in U.S. patent appln. Ser. No. 09/82,110, filed May 20, 1998 and U.S. patent appln. Ser. No. 08/841,466, filed Apr. 22, 1997, both of which applications are assigned to the same assignee as the present application.

Figure 2:
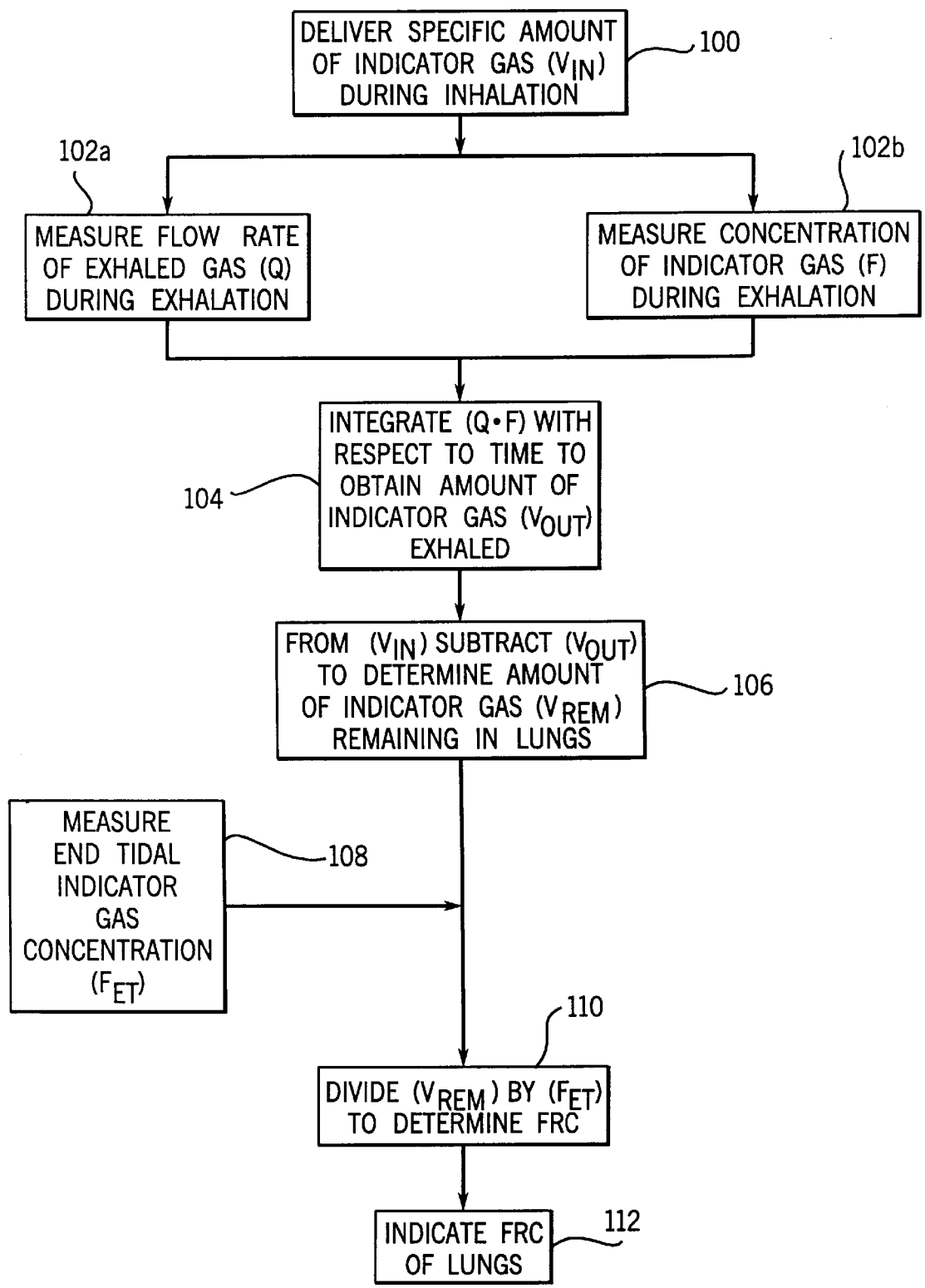
FIG. 2 is a flow chart illustrating certain operative principles employed in the method of the present invention.

FIG. 2 is a simplified flow chart that will assist in understanding the method of the present invention. The explanation of the flow chart employs the apparatus of FIG. 1. In step 100, functional residual capacity measuring circuit 54 operates dosing device 50 to provide a specific volumetric amount of indicator gas ($V_{in}$) into the gases inhaled by the subject during the inhalation phase of a respiratory cycle.

At the conclusion of the inhalation phase of the breathing cycle, the subject exhales gases from his/her lungs 10. In respirator 14, inhalation valve 32 is closed and exhalation valve 34 is opened. The amount of indicator gas exhaled upon exhalation by the subject can be measured by integrating the product of instantaneous gas flow (Q) in breathing tube 12 and the corresponding indicator gas concentration (F) occurring during exhalation.

The product of the instantaneous flow rate and instantaneous indicator gas concentration is integrated with respect to time in step 104 to obtain the amount of indicator gas ($V_{out}$) exhaled by the patient.

Subtraction of the amount of the indicator gas ($V_{out}$) exhaled by the subject from the amount of indicator gas ($V_{in}$) inhaled by the patient gives the amount of indicator gas ($V_{rem}$) remaining in the lungs of the subject at the end of exhalation, i.e., the amount of indicator gas in the subject's functional residual capacity (FRC).

The concentration of the indicator gas existing at the end of exhalation, i.e. the end-tidal concentration is measured in step 106, as by measuring device 46. The physiology of the lungs is such that the end-tidal of concentration of indicator gas in the exhaled gases of the subject is the same as, or very close to, the concentration of indicator gas in lungs 10 of the subject.

Since the end-tidal concentration of the indicator gas is the same as the concentration of indicator gas in the lungs of the patient, the functional residual capacity of the lungs can be determined by dividing the volume of indicator gas remaining in the subject's lungs, as determined in step 106, by the end-tidal indicator gas concentration, as determined in step 108. See step 110. The functional residual capacity of the lungs is indicated at step 112.

The foregoing steps thus determine the functional residual capacity of the patient's lungs in accordance with Equation 3, above.

The flow chart of FIG. 2 shows a simplified, single breath, "wash-in" technique in which indicator gas is supplied to the breathing gases during the subject's breathing.

Figure 3A:
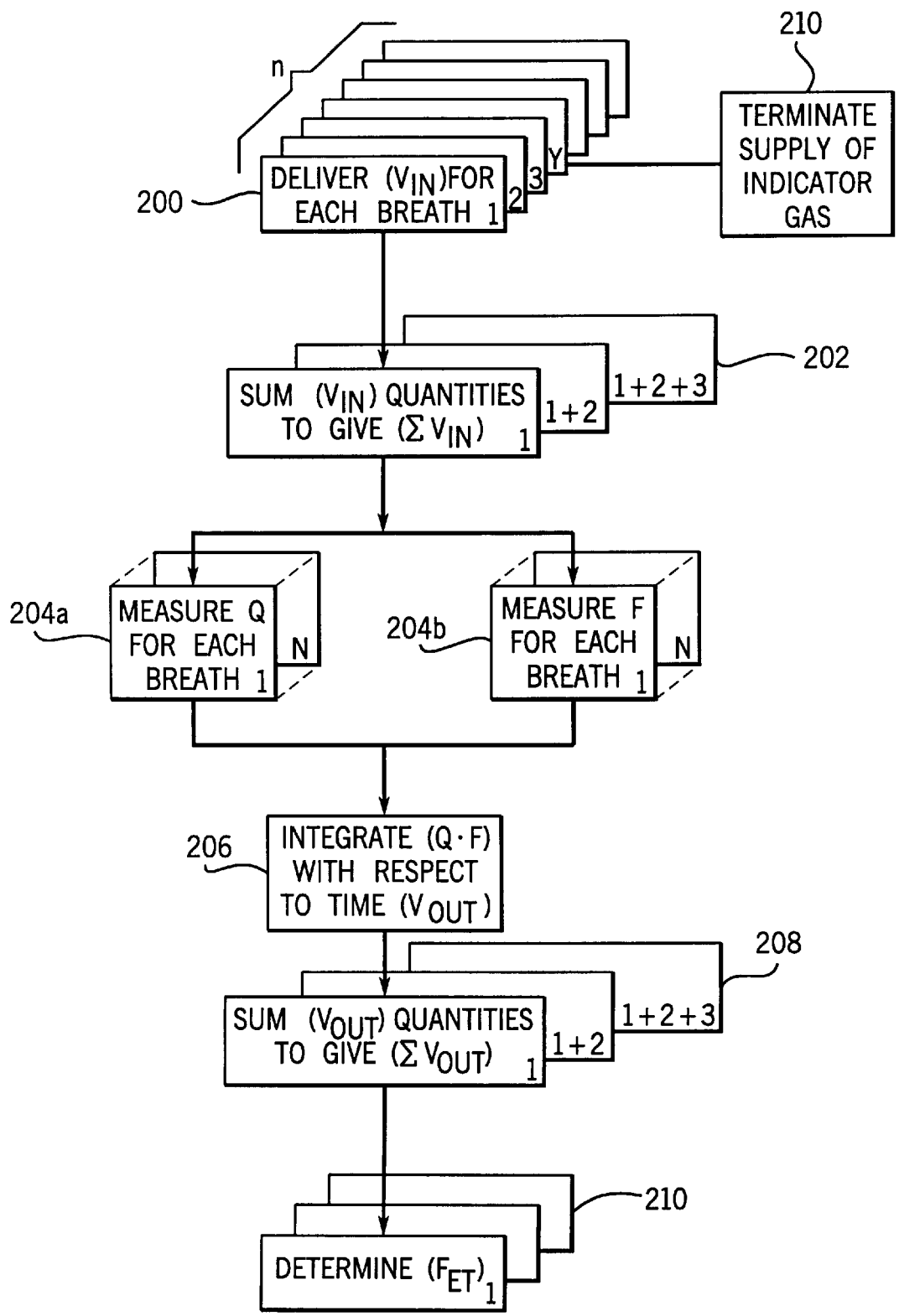
FIGS. 3A and B is a flow chart showing the steps of the method of the present invention.

FIGS. 3A and B more particularly show the method of the present invention, which method utilizes a plurality of sequential breathing cycles of the patient to obtain accurate functional residual capacity measurement. FIGS. 3A and B show both a wash-in phase and a wash-out phase.

For repetitive breaths of the patient, Equation 3 becomes $$FRC_{in} = \frac{\sum_{i=1}^{n} V_{in} - \sum_{i=1}^{n} \int F \times Q \times dt}{F_{ET}} \quad (4)$$

where $F_{ET}$ is the difference between the end-tidal concentration at the beginning of the functional residual capacity determination and the end-tidal concentration at the end of the functional residual capacity determination.

In the method shown in FIGS. 3A and B, a specific amount of indicator gas ($V_{in}$) is typically delivered during a plurality of inhalations by the subject in step 200. As noted above, this is preferably in the form of a discrete dose or pulse of indicator gas. The administration of the specific volumetric amount of indicator gas may be accomplished responsive to a signal from a sensor, such as sensor 40, in breathing tube 12 indicating inhalation by the subject or responsive to a signal from control 30 indicating that inhalation valve 32 is being opened to provide breathing gases to inhalation limb 16 and breathing tube 12. As noted above, when sulfurhexafluorine ($SF_6$) is used as the indicator gas, the amount of indicator gas provided can be small, for example, an amount sufficient to provide a concentration of 0.5% or less in the gases found in the functional residual capacity of the subject. ($\Sigma V_{in}$)

The amount provided in any given breath is added to the sum of the amounts delivered during the inhalation phases of previous breaths by the patient to form the total amount of indicator gas quantity ($\Sigma V_{in}$) for n breaths. Thus, the amount of gas delivered during the second breath (2) is added to the quantity of gas delivered in the first breath (1); the amount of indicator gas supplied during the third breath (3) is added to the sum of the amounts of indicator gas provided in breaths 1 and 2, etc. The summation process is carried out for each breath, in the cumulative, sequential breaths, i.e. for breath 1, for breaths 1 and 2, for breaths 1, 2 and 3, etc., to provide a $\Sigma V_{in}$ value for breath 1, for breaths 1 and 2, etc. The summation producing the plurality of $\Sigma V_{in}$ values is shown in step 202.

The amount of indicator gas added during each breath can be the same. Or, the added amount of indicator gas can vary in successive breaths.

The amount of indicator gas contained in the breathing gases exhaled by the patient in each breath is determined in steps 204a, 204b, and 206, which steps are analogous to steps 102a, 102b, and 104 shown in FIG. 2. To this end, the flow rate of the exhaled gases and the concentration of the indicator gas in the exhaled gases of the subject are measured at steps 204a and 204b. The measurement of flow rate is carried out by flow sensor 40 and flow rate circuitry 42. The measurement of the concentration of the indicator gas is carried out by concentration measuring device 46. The integration in step 206 may be carried out by appropriate circuitry in functional residual capacity measuring circuit 54. The result of these steps is the amount of indicator gas $V_{out}$ exhaled during each breath.

In a manner similar to step 202, in step 208, the amount of indicator gas exhaled in any given breath is added to the sum of amounts of indicator gas exhaled during previous exhalations to form a quantity ($\Sigma V_{out}$) indicative of the total amount of indicator gas exhaled by the subject for n breaths. Specifically, the summation process is carried out for each breath in the cumulative sequence of breaths. That is, the amount of indicator gas exhaled in the first breath is determined, the sum of the amounts of indicator gases exhaled in breaths 1 and 2 is determined, the sum of the amounts of indicator gases exhaled in breaths 1, 2, and 3 is determined, etc. This provides a $\Sigma V_{out}$ value for the first breath, for breaths 1 and 2, etc.

As noted above, FIGS. 3A and B show an embodiment of the invention having both a wash-in phase and a subsequent wash-out phase. In the wash-out phase, the supply of indictor gas to the subject is terminated, i.e. $V_{in}$ becomes zero, as at step 210. This may occur at breath y shown in FIG. 3A. With the supply of indicator gas terminated, the total amount of indicator gas ($\Sigma V_{in}$) supplied to the subject thereafter remains unchanged since zero volume of indicator gas is added to ($\Sigma V_{in}$).

In succeeding breaths after termination of the indicator gas supply, the indicator gas will wash out of the functional residual capacity of the subject. The amount of indicator gas in the exhaled breathing gases of the subject continues to be measured in steps 204a, 204b, and 206 and summed in step 208. The number of breaths may be such that at the end of the test, the lungs of the subject are free of indicator gas; that is, all the indicator gas supplied to the lungs of the subject has been removed from the lungs of the subject.

Integrating the product of gas flow rate Q and instantaneous indicator gas concentration F with respect to time over both the wash-in and wash-out phases, thus starting from, and ending with, indicator gas free lungs, the inhaled amount of indicator gas and the exhaled amount of indicator gas should be the same or $$\Sigma V_{in} - \Sigma \int F \times Q \times dt = 0 \quad (5)$$

Due to various inaccuracies, such as improper time synchronization of the exhaled breathing gas flow and concentration measurement and in exhaled volume integration, or leakage of breathing gases out of the breathing circuit, the sum of the incremental determinations of indicator gas exhaled ($\Sigma V_{out}$) and the supplied amounts of indicator gas ($\Sigma V_{in}$) would not in fact equal zero. A factor K can be inserted in Equation 5 to reflect the presence of any such errors and make the difference between the two quantities zero. In the absence of any such errors, factor K would be unity. Equation 5 thus becomes $$\Sigma V_{in} - K \times \Sigma \int F \times Q \times dt = 0 \quad (6)$$

In step 210, the concentration of indicator gas in the subject's lungs is determined, as by using end tidal concentrations in the exhaled gases of the subject. As noted in the discussions of Equations 2 and 4, the quantity $F_{ET}$ is the difference between the concentration at the beginning of the functional residual capacity determination and the concentration at the end of the sequence of breaths used in functional residual capacity determination. If the functional residual capacity determination begins with zero indicator gas concentration in the subject's lungs, the quantity $F_{ET}$ will be the indicator gas concentration at the end of the sequence of breaths used in the determination. Otherwise, the quantity $F_{ET}$ is the difference between the concentration at the first breath of the sequence of breaths and the concentration at the last breath of the sequence.

The determination of indicator gas concentration $F_{ET}$ in the lungs of the subject is thus correctly correlated to the $\Sigma V_{in}$ and $\Sigma V_{out}$ quantities used for determining functional residual capacity. The result is a plurality of $\Sigma V_{in}$, $\Sigma V_{out}$, and $F_{ET}$ data sets, i.e. a data set for the first breath, a data set for breaths 1 and 2, a data set for breaths 1, 2, and 3 for the breaths used to determine functional residual capacity.

Factor K is inserted into Equation 4 to enable the method of the present invention to be used, for example, with imperfectly sealed breathing masks in spontaneously breathing subjects or with pediatric patients where leaks occur through unsealed intubation tubes. In both such situations, some of the exhaled indicator gas is lost. Equation 4 as expressed over the integration for both the wash-in and wash-out phases becomes $$FRC_n \times F_{ET} + K \times \sum_{i=1}^{n} \int F \times Q \times dt = \sum_{i=1}^{n} V_{in} \quad (7)$$

For purposes of explanation and as indicated in step 212, Equation 7 can be simplified to $$\Sigma V_{in} = FRC \times F_{ET} + K \times \Sigma V_{out} \quad (8)$$

in which form it can be seen to clearly define a linear surface equation of the type $$y = b_1 x_1 + b_2 x_2 \quad (9)$$

In equation 9, the terms y, $x_1$ and $x_2$ are known variables and $b_1$ and $b_2$ are regression coefficients, i.e. terms expressing the amount by which $x_1$ or $x_2$ must be multiplied to give a corresponding change in y, or, conversely, the amount y changes for a unit change in $x_1$ or $x_2$. In this way, these coefficients represent the degree to which a line showing the relationship between y and $x_1$ or y and $x_2$ in a two dimensional graph slopes upwards or downwards.

In the case of equations 7 and 8, $\Sigma V_{in}$, $\Sigma V_{out}$, and $F_{ET}$ are the measured variables and K and FRC are regression coefficients to be determined. Using two dimensional regression analysis, and at least two sets of $\Sigma V_{in}$, $\Sigma V_{out}$, and $F_{ET}$ data, as determined in steps 202, 208, and 210, best fit values for each of K and FRC can be obtained as, for example, on a least squares fit basis in step 214. Using additional sets of $\Sigma V_{in}$, $\Sigma V_{out}$, and $F_{ET}$ values from steps 202, 208, and 210, in such regression analysis and fitting will improve the accuracy of the best fit values for K and FRC.

Figure 4:
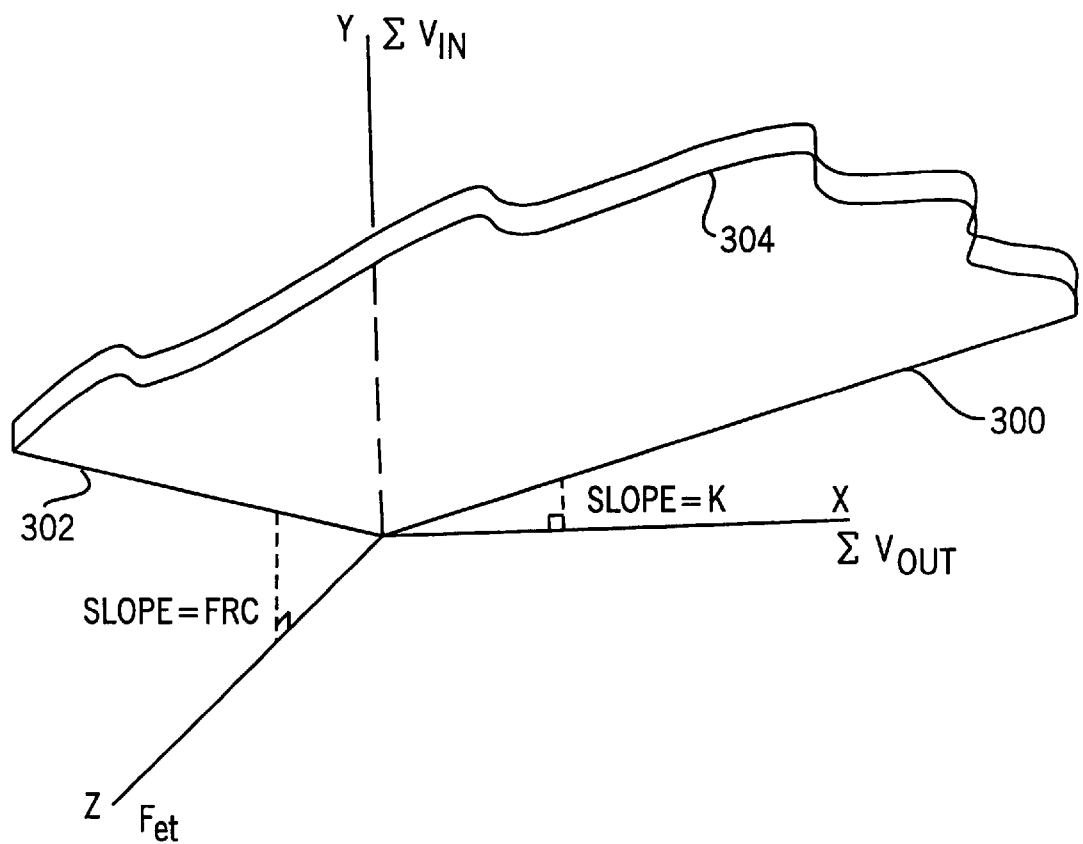
FIG. 4 is an orthogonal axis spatial system graphically showing the manner in which functional residual capacity is determined by the method of the present invention.

The manner in which the foregoing is carried out can be appreciated in a simplified form by the graphic explanation shown in FIG. 4. FIG. 4 shows a three orthogonal axis spatial system in which $\Sigma V_{in}$, $\Sigma V_{out}$, and $F_{ET}$ form the coordinate axes x, y, and z, respectively. The x-y plane contains the relationship of $\Sigma V_{in}$ to $\Sigma V_{out}$, and, hence, contains an expression of the K regression coefficient defining the relationship between these quantities as the slope of line 300 appearing in that plane. The z-y plane shows the relationship of $\Sigma V_{in}$ to $F_{ET}$ and, hence, contains an expression of the FRC regression coefficient defining the relationship between these quantities as the slope of line 302.

The graphic derivation of the coefficients K and FRC can be appreciated from FIG. 4, as follows. The plurality of sets of measured variables, end tidal indicator gas concentration $F_{ET}$, the total exhaled gas volume ($\Sigma V_{out}$), i.e. $\Sigma \int F \times Q \times dt$, and the total inhaled indicator gas amount ($\Sigma V_{in}$) for each cumulative breath 1 through n identifies a plurality of points in the x,y,z spatial system. Since the spatial system of FIG. 4, is three dimensional, a plane, shown in FIG. 4 as 304, rather than a line, is fitted to the data points identified in the spatial system on at least squares basis. This plane is the linear surface defined by equations 7 and 8.

The intercept of plane 304, so fitted to the data points, in the x-y plane forms line 300, the slope of which is the regression coefficient K. The intercept of plane 304 in the z-y plane forms line 302, the slope of which is the regression coefficient FRC and hence the functional residual capacity of the subject's lungs provided in step 214.

It is recognized, that at the end of an exhalation, there is a volume remaining in the lungs and the high airways of the subject that form an anatomical dead space filled with the mixture of the indicator gas and breathing gas. Because the amount of indicator gas in the lungs is determined as the difference between the amount inhaled and the amount exhaled, the amount of indicator gas in the lungs will include that in the anatomical dead space. Functional residual capacity determined in the above manner usually includes the effect of this anatomical dead space. If true lung functional residual capacity is required, the anatomical dead space volume, which is typically constant and depends on the size of the subject, can be subtracted from the functional residual capacity value determined in the above manner, as shown in step 216, to provide functional residual capacity excluding such dead space volume.

The final determination of functional residual capacity is indicated at step 218.

For clarity in the derivation of Equation 7, it was assumed that the wash-in and wash-out periods start from, and end with, a zero indicator gas concentration in the lungs of the subject and in the end tidal breathing gases. However, in using a plurality of breaths, Equation 7 can be utilized to establish measured value data points using any sequence of breaths in the total series of cumulative breaths 1 through n and for which the beginning and ending end tidal indicator gas concentration will not necessarily be zero.

It will be appreciated that with the use of the factor K described in connection with Equation 6, the determination of the exhaled volume of the indicator gas in steps 204a, 204b and 206 does not need to be completely accurate since the magnitude of factor K is altered to compensate for any inaccuracies and, particularly, those of a constant nature arising, for example, from leakage or time synchronization errors between flow and concentration measurement.

The foregoing can be seen by reference to Equation 7. Assume that the pneumatic pressure generated during exhalation causes a subject's breathing face mask to leak exhalation gases. The quantity $\Sigma V_{out}$ will decrease because of the leaks. However, the Equation 7 quantities FRC, $F_{ET}$, and $\Sigma V_{in}$ will be unaffected by the leakage of exhalation gases. In Equation 7, as $\Sigma V_{out}$ decreases, the factor K will increase in order to maintain the equality expressed in the equation. In the graphic explanation of FIG. 4, the reduction of $\Sigma V_{out}$ will move the data points used to establish plane 304 along the x axis toward the origin, increasing the slope of line 300 and the magnitude of factor K.

Thus, the determination of functional residual capacity by the method of the present invention avoids, or is less sensitive to, inaccuracies due to leakage, synchronization errors, and the like.

Use of the factor K can further simplify the determination of the amount of exhaled indicator gas ($\Sigma V_{out}$). For example, if the succession of breaths used to determine functional residual capacity is characterized by a constant volume of expired breathing gas, as when ventilator 14 is in use, the quantity $K \times \Sigma \int F \times Q \times dt$ found in Equation 7 can be simplified to $K^1 \times \Sigma F_{ET}$.

That is, the constant volume of exhaled breathing gas is reflected in the altered factor K'. Use of this simplification avoids the need to obtain the flow measure Q and the corresponding concentration measurement F so that Equation 7 becomes $$FRC \times F_{ET} + K^1 \times \Sigma F_{ET} = \Sigma V_{in} \quad (10)$$

Figure 3B:
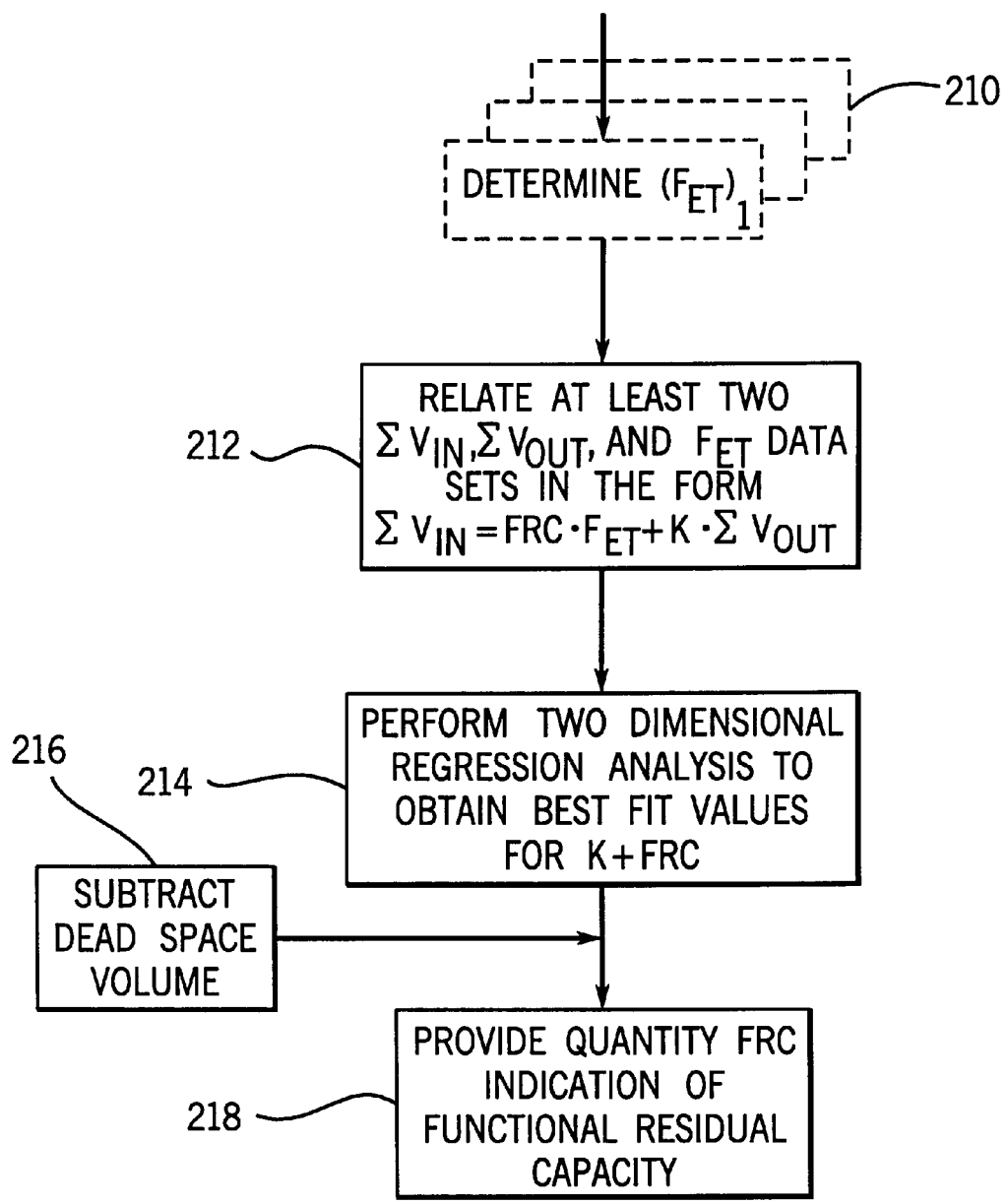

In FIG. 3, step 204a can be eliminated and step 204b becomes a measurement of end tidal indicator gas concentration $F_{ET}$. In FIG. 1, while flow sensor 40 could also be eliminated, it is preferable to retain same as a means for sensing the commencement of inhalation and to trigger the supply of doses of the indicator gas.

Another simplification in a generally steady state circumstance is to use the quantity $K^{11} \times \Sigma V_{EXP} \times F_{ET}$ as the exhaled indicator gas quantity. $V_{exp}$ is the amount of breathing gas exhaled by the subject. The foregoing quantity can be used when the amount of breathing gas exhaled by the subject is relatively predictable or can be made predictable as, for example, by subtracting an estimated anatomical dead space from the amount of breathing gases exhaled by the subject so as to minimize variations in $V_{exp}$ as a result of variations in the volume of the anatomical dead space.

An alternate method of determining the FRC is as follows. Instead of utilizing the cumulative sum of the volume of indicator gas delivered during a series of breaths, the derivative of the cumulative sum can be used to determine the volume of indicator gas delivered during each individual breath. Likewise, instead of the cumulative sum of the volume of indicator gas exhaled, a derivative is taken to determine the volume of gas exhaled during each breath. In this situation, instead of the indicator gas concentration, the difference ($\Delta F_{ET}$) in concentration of the indicator gas between the given breath and the breath immediately preceding is determined.

When utilizing the derivative values for each breath in accordance with the alternate method described above, Equation 8 becomes $$\Delta F_{ET} \times FRC = V_{in} - K'V_{out} \quad (11)$$

A data set, including data points $V_{in}$, $V_{out}$ and $\Delta F_{ET}$, for each given breath can be measured and multiple data sets, each of which are taken during a single breath preceding the given breath, can be used to determine K and FRC by using multiple regression analysis as previously discussed. In the alternate embodiment, the measured values $V_{out}$, $V_{in}$, and $\Delta F_{ET}$ represent the x, y, and z axes, respectfully, in FIG. 4.

In yet another alternate method to determine K and FRC, the indicator gas can initially be washed into the patient's lungs until a steady state exists within the lungs. Once a steady state is achieved, the $F_{et}$ becomes a constant for subsequent breaths and the $V_{out}$ is equal to the $V_{in}$. Since the correction factor K is related to the amount of indicator gas lost, the value K can be solved from the one dimensional regression Vin=K×Vout. Once the K factor has been determined as described, the K factor can be used to solve the FRC from the data sets collected during the wash-in and/or wash-out phases. The solution of FRC with the already known K is a one dimensional regression $$F_{ET} \times FRC = \Sigma V_{in} - K \times \Sigma V_{out} \quad (12)$$

or if the derivative method set out above is used and data sets collected for each individual breath $$\Delta F_{ET} \times FRC = V_{in} - K \times V_{out} \quad (13)$$

I claim:

1. A method for determining functional residual capacity (FRC) of the lungs of a subject, the subject having sequential breaths, each with an inhalation and an exhalation, said method comprising the steps of:

providing breathing gas or gases to the subject, the breathing gas or gases flowing into the lungs of the subject during inhalations, exhalation gases flowing from the subject during exhalations;

delivering a given amount of indicator gas into the breathing gas or gases flowing into the lungs of the subject during inhalation by the subject in at least one breath of a number of sequential breaths selected for determining functional residual capacity;

summing the amounts of indicator gas delivered during the selected number of breaths to provide, for at least two given breaths in the selected number, the cumulative total of the amounts indicator gas delivered in the given breath and in all breaths preceding the given breath in the selected number of sequential breaths ($\Sigma V_{in}$)

determining a quantity representative of the amount of indicator gas removed from the lungs of the subject during exhalations by the subject in each breath of the number of sequential breaths;

summing the quantities representative of the amounts of indicator gas removed from the lungs of the subject during the selected number of breaths to provide, for said at least two given breaths in the selected number, the cumulative total of the amounts indicator gas removed in the given breath and in all breaths preceding the given breath in the selected number of sequential breaths ($\Sigma V_{out}$)

obtaining an indication of the concentration of indicator gas in the lungs of the subject ($F_{ET}$)for said at least two given breaths and resulting from the delivery and removal of the indicator gas amounts summed in said cumulative totals for said at least two given breaths;

using the quantities $\Sigma V_{in}$, $\Sigma V_{out}$, and $F_{ET}$ as measured variables to form at least two measured value data sets in which the quantities are related by regression coefficients such that the product of the indicator gas concentration ($F_{ET}$) and a first regression coefficient comprising the functional residual capacity (FRC) plus the product of the cumulative total of indicator gas removed from the subject's lungs ($\Sigma V_{out}$) and a second regression coefficient K equals the cumulative total of the delivered indicator gas ($\Sigma V_{in}$); and using said at least two measured value data sets and the relationship between $\Sigma V_{in}$, $\Sigma V_{out}$ and $F_{ET}$ to obtain values for K and FRC, the value FRC so obtained being a determination of the functional residual capacity of the lungs of the subject.

2. The method of claim 1 further comprising the steps of:

delivering the indicator gas into the lungs of the subject until a steady state exists within the lung such that the concentration of indicator gas ($F_{ET}$) in the lungs of the subject is constant for each subsequent breath in the number of sequential breaths;

using the quantities $V_{in}$ and $V_{out}$ as measured variables to determine the second regression coefficient K which is the quotient of the $V_{in}$ and $V_{out}$ ; and using the determined value of the second regression coefficient K and said at least two measured value data sets to perform a one-dimensional regression to determine the first regression coefficient FRC.

3. The method according to claim 1 wherein the step of determining K and FRC includes the step of carrying out a multi-dimensional regression analysis using said at least two data sets to obtain values for K and FRC fitted to said data sets.

4. The method according to claim 3 wherein the step of delivering the indicator gas is further defined as delivering a given amount of indicator gas in a plurality of breaths of the number of sequential breaths.

5. The method according to claim 3 wherein the step of delivering the indicator gas is further defined as delivering the indicator gas in said at least one breath and thereafter terminating the delivery of indicator gas for the remaining breaths of the selected number of sequential breaths.

6. The method according to claim 4 wherein the step of delivering the indicator gas is further defined as delivering the indicator gas in said at least one breath and thereafter terminating the delivery of indicator gas for the remaining breaths of the selected number of sequential breaths.

7. The method according to claim 4 wherein the step of delivering a given amount of indicator gas is further defined as delivering a similar amount of indicator gas during the plurality of breaths.

8. The method according to claim 4 further defined as delivering the differing amounts of indicator gas during the plurality of breaths.

9. The method according to claim 3 wherein the step of delivering the indicator gas is further defined as delivering a discrete dose of indicator gas to the breathing gas or gases flowing to the subject.

10. The method according to claim 9 wherein the step of delivering the indicator gas is further defined as delivering the indicator gas in the form of a pulse of indicator gas.

11. The method according to claim 9 wherein the step of delivering the indicator gas is further defined as delivering the indicator gas by opening and closing a valve.

12. The method according to claim 3 wherein the step of delivering the indicator gas is further defined as delivering an amount of indicator gas sufficient to establish a concentration of 1.0% or less in the breathing gas or gases flowing to the subject.

13. The method according to claim 3 wherein the step of delivering the indicator gas is further defined as delivering an amount of indicator gas sufficient to establish a concentration of 0.5% or less in the breathing gas or gases flowing to the subject.

14. The method according to claim 3 wherein the step of delivering the indicator gas is further defined as delivering an indicator gas comprising sulfurhexafluoride ($SF_6$).

15. The method according to claim 3 wherein the step of delivering the indicator gas is further defined as synchronizing the start of the delivery with the commencement of inhalation by the subject and terminating the delivery of the indicator gas before inhalation stops.

16. The method according to claim 3 wherein the step of delivering the indicator gas is further defined as delivering the indicator gas in proximity to the lungs of the subject.

17. The method according to claim 3 wherein the step of determining a quantity representative of the removed amount of indicator gas is further defined as determining the amount of indicator gas removed from the lungs of the subject during exhalation.

18. The method according to claim 17 wherein the step of determining the removed amount of indicator gas is further defined as determining the amount by measurement of the exhalation gas flow and concentration of indicator gas during exhalation.

19. The method according to claim 18 wherein the step of determining the removed amount of indicator gas is further defined as measuring the exhalation gas flow and corresponding concentration of indicator gas during exhalation and integrating the product of the instantaneous gas flow and indicator gas concentration measurements.

20. The method according to claim 3 wherein the exhaled amount of breathing gas or gases is generally constant and wherein the step of determining a quantity representative of the removed amount of indicator gas is further defined as obtaining the amount from the concentration of indicator gas in the lungs of the subject.

21. The method according to claim 3 wherein the amount of breathing gas or gases exhaled by the subject is a predictable quantity and wherein the step of determining a quantity representative of the amount of indicator gas removed from the lungs of the subject is further defined as employing the concentration of indicator gas in the lungs of the subject and the amount of breathing gas exhaled by the subject.

22. The method according to claim 3 wherein the step of obtaining the indication of indicator gas concentration in the lungs of the subject is further defined as measuring the indicator gas concentration in the end tidal exhalation gases of the subject.

23. The method according to claim 3 wherein the step of obtaining the indicator gas concentration indication is further defined as determining the difference between the indicator gas concentration at the beginning of the selected number of sequential breaths and the indicator gas concentration at the end of the selected number of sequential breaths.

24. The method according to claim 3 wherein the step of carrying out a multi-dimensional regression analysis is further defined as obtaining values for K and FRC fitted to said data sets on a least squares basis.

25. The method according to claim 3 further defined as including the step of compensating the functional residual capacity determination for anatomical dead spaces in respiratory organs of the subject.

26. A method for determining functional residual capacity (FRC) of the lungs of a subject, the subject having sequential breaths, each with an inhalation and an exhalation, the method comprising the steps of:

providing breathing gas or gases to the subject, the breathing gas or gases flowing into the lungs of the subject during inhalations, exhalation gases flowing from the subject during exhalations;

delivering a given amount of indicator gas into the breathing gas or gases flowing into the lungs of the subject during inhalation by the subject in at least one breath of a number of sequential breaths for determining the functional residual capacity;

summing the amount of indicator gas delivered in a measurement period between a given breath and a previous, reference breath to provide an amount of indicator gas delivered in the measurement period ($V_{in}$);

determining a quantity representative of the amount of indicator gas removed from the lungs of the subject during exhalation by the subject;

summing the quantities representative of the amount of indicator gas removed from the lungs during the measurement period between the given breath and the reference breath to provide an amount of indicator gas removed from the lungs in the measurement period ($V_{out}$);

obtaining an indication of the concentration of indicator gas in the lungs of the subject ($F_{ET}$) for the given breath;

subtracting the concentration of indicator gas in the lungs of the subject ($F_{ET}$) for the previous reference breath from the concentration of the indicator gas in the lungs of the subject ($F_{ET}$) for the given breath to determine a differential concentration of indicator gas in the lungs of the subject in the measurement period ($\Delta F_{ET}$);

using the quantities $V_{in}$, $V_{out}$, and $\Delta F_{ET}$ from at least two measurement periods to form at least two measured value data sets as measured variables in which the quantities are related by regression coefficients such that the product of the differential concentration of indicator gas ($\Delta F_{ET}$) and a first regression coefficient comprising the functional residual capacity (FRC) plus the product of the volume of indicator gas removed from the subject's lungs ($V_{out}$) and a second regression coefficient K equals the volume of the delivered indicator gas ($V_{in}$); and using the at least two measured value data sets and the relationship between $V_{in}$, $V_{out}$, and $\Delta F_{ET}$ to obtain values for K and FRC, the value FRC so obtained being a determination of the functional residual capacity of the lungs of the subject.

27. The method of claim 26 further comprising the steps of:

delivering the indicator gas into the lungs of the subject until a steady state exists such that the concentration of indicator gas ($F_{ET}$) in the lungs of the subject is constant for each breath;

using the quantities $V_{in}$ and $V_{out}$ as measured variables to determine the second regression coefficient K which is the quotient of the $V_{in}$ and $V_{out}$; and using the determined value of K and said at least two measured value data sets to perform a one-dimensional regression to determine said first regression coefficient FRC.

28. The method according to claim 26 wherein the step of determining K and FRC includes the step of carrying out a multi-dimensional regression analysis using said at least two data sets to obtain values for K and FRC fitted to said data sets.

29. The method of claim 28 wherein the reference breath is the breath immediately preceding the given breath such that the measurement period is between the given breath and the breath immediately preceding the given breath.

30. The method according to claim 29 further defined as delivering the differing amounts of indicator gas during a plurality of sequential breaths.

31. The method according to claim 26 wherein the step of delivering the indicator gas is further defined as delivering a discrete dose of indicator gas to the breathing gas or gases flowing to the subject.

32. The method according to claim 31 wherein the step of delivering the indicator gas is further defined as delivering the indicator gas in the form of a pulse of indicator gas.

33. The method according to claim 31 wherein the step of delivering the indicator gas is further defined as delivering the indicator gas by opening and closing a valve.

34. The method according to claim 26 wherein the step of delivering the indicator gas is further defined as delivering an indicator gas comprising sulfurhexafluorine ($SF_6$).

35. The method according to claim 26 wherein the step of delivering the indicator gas is further defined as synchronizing the start of the delivery with the commencement of inhalation by the subject and terminating the delivery of the indicator gas before inhalation stops.

36. The method according to claim 29 wherein the step of carrying out a multi-dimensional regression analysis is further defined as obtaining values for K and FRC fitted to said data sets on a least squares basis.

37. The method according to claim 29 further defined as including the step of compensating the functional residual capacity determination for anatomical dead spaces in respiratory organs of the subject.

* * * * *